United States Patent [19]

Knowles et al.

[11] 4,119,652

[45] Oct. 10, 1978

[54] CATALYTIC ASYMMETRIC HYDROGENATION

[75] Inventors: William S. Knowles, St. Louis; Milton J. Sabacky, Ballwin, both of Mo.

[73] Assignee: Monsanto Company, St. Louis, Mo.

[21] Appl. No.: 700,254

[22] Filed: Jun. 25, 1976

Related U.S. Application Data

[60] Continuation of Ser. No. 501,555, Aug. 29, 1974, abandoned, which is a division of Ser. No. 173,620, Aug. 20, 1971, Pat. No. 3,849,480, which is a continuation of Ser. No. 758,603, Sep. 9, 1968, abandoned.

[51] Int. Cl.² .................................... C07F 15/00
[52] U.S. Cl. ............................... 260/429 R; 260/645; 260/668 R; 260/683.9; 260/958; 260/962; 252/431 P; 252/431 N; 260/270 PY; 260/27 DR; 260/313.1; 260/326.61; 260/329 ME; 260/346.1; 260/347.7; 260/347.8; 260/347.91; 260/568; 260/583 R; 260/586 R; 260/607 R; 260/609 R; 260/644; 562/592; 562/606; 562/496
[58] Field of Search ........ 260/429 R, 270 PY, 270 R, 260/313.1, 326.61, 329 ME, 346.1 M, 441

[56] References Cited

U.S. PATENT DOCUMENTS

| 3,409,599 | 11/1968 | Bauer et al. | 260/429 R |
|---|---|---|---|
| 3,458,547 | 7/1969 | Coffey | 260/429 R |
| 3,489,786 | 1/1970 | Dewhirst | 260/429 R |
| 3,639,439 | 2/1972 | Dewhirst | 260/429 R |

OTHER PUBLICATIONS

Chatt et al., J. Chem. Soc. 1963, pp. 3371-3374.
Brookes et al. J. Chem. Soc. (A), 1967, pp. 1079-1084.
Jenkins et al., J. Chem. Soc. 1965, pp. 6789-6796.
Brookes et al., Chem. Abstracts 1967, vol. 67 #69276.
Dewhirst et al., Chem. Abstracts 1968, #74747.

*Primary Examiner*—Helen M. S. Sneed
*Attorney, Agent, or Firm*—Robert E. Wexler; Howard C. Stanley; Edward P. Grattan

[57] ABSTRACT

Process for the homogeneous catalytic hydrogenation of olefins, capable of existing as enantiomorphs upon hydrogenation of the olefinic bond, which yields on hydrogenation an optically active mixture. The process comprises the hydrogenation of the olefin in the presence of an optically active coordinated metal hydrogenation catalyst, in which the metal is selected from the group consisting of rhodium, iridium, ruthenium, osmium, palladium and platinum.

This process is a generalized process for any asymmetric hydrogenation of olefins in which one optical enantiomorph is desired. It is also a generalized process for the selective hydrogenation of olefins in the presence of other reactive groups which are easily hydrogenated. It is especially useful for the preparation of natural products which possess optical activity, such as amino acids, and for products such as flavors, fragrances which may require optical activity for their utilitization.

This invention also relates to new optically active coordinated hydrogenation catalysts.

7 Claims, No Drawings

CATALYTIC ASYMMETRIC HYDROGENATION

This is a continuation of application Ser. No. 501,555, filed Aug. 29, 1974, now abandoned, which is a division of application Ser. No. 173,620, filed Aug. 20, 1971, now issued as U.S. Pat. No. 3,849,480 on Nov. 19, 1974, which is a continuation of application Ser. No. 758,603, filed Sept. 9, 1958, now abandoned.

When an olefin, which in its saturated form is optically active, is hydrogenated, the usual resultant product is optically inactive mainly because an equal amount of both optical antipodes (racemic mixture) are formed. To obtain the desired optical antipode, the mixture must be separated into its optical components. This procedure is laborious, expensive, and often results in destruction of the undesired optical antipode. Due to these difficulties, increased attention has been placed on asymmetric snythesis in which one of the enantiomorphs is obtained in major amounts.

It has now been found that olefinic bonds can be selectively hydrogenated, in the presence of an optically active coordinated metal hydrogenation catalyst, to yield an optically active compound, according to the following equation:

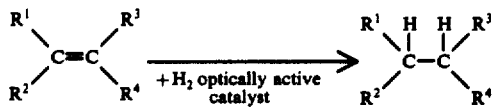

wherein $R^1$, $R^2$, $R^3$ and $R^4$ are each independently selected from the group consisting of hydrogen, alkyl, having at least one and a maximum of 12 carbon atoms, substituted alkyl said substitution being selected from the group consisting of amino, hydroxy, nitro, thio, carbonyl carboxyl, carboxylic ester, said ester group having a maximum of 6 carbon atoms, phenyl, substituted phenyl, said substitution being selected from the group consisting of alkyl having a maximum of 4 carbon atoms, amino, carboxyl, nitro and carboxylic ester, said ester having a maximum of 4 carbon atoms and said substitution being less than 3 substituents, amino, benzylamino, dibenzylamino, nitro, carboxyl and carboxylic ester, said ester having a maximum of 4 carbon atoms, provided that at least one of the ethylenic carbons on hydrogenation is asymmetric.

The groups $R^1$, $R^2$, $R^3$ and $R^4$ may also have an asymmetric carbon. This would not prevent the formation of an additional asymmetric carbon on hydrogenation.

The optically active hydrogenation catalyst used in this invention is a coordination complex of a metal selected from the group consisting of rhodium, iridium, ruthenium, osmium, palladium and platinum, with a phospine or arsine moiety of the formula $AR^5R^6R^7$ wherein A is phosphorus or arsenic and $R^5$, $R^6$, and $R^7$ are each independently selected from the group consisting of hydrogen, alkyl, having at least one carbon atom and a maximum of 12 carbon atoms, substituted alkyl, said substitution selected from the group consisting of amino, carbonyl, phenyl, nitro and alkoxy, said alkoxy having a maximum of 4 carbon atoms, phenyl, substituted phenyl, said substitution selected from the group consisting of alkyl having a maximum of 4 carbon atoms, amino and nitro, said substitution being less than 3 substituents, cycloalkyl having at least 3 carbon atoms and a maximum of 6 carbon atoms, pyrryl, thienyl, furyl, pyridyl and piperidyl. At least one of the moieties $AR^5R^6R^7$ must be optically active.

Optical activity of the metal coordinated complex, according to this invention, resides in the phosphine or arsine moiety. This optical activity may result either from having three different groups on the phosphorus or arsenic atom or by having an optically active group attached to the phosphorus or arsenic atom.

The coordination complex is represented by the formula $M^1X_nL_3$ or $M^2X_2L_2$ wherein $M^1$ is a metal selected from the group consisting of rhodium, iridium, ruthenium and osmium; $M^2$ is selected from the group consisting of palladium and platinum; X is selected from the group consisting of hydrogen, fluorine, bromine, chlorine and iodine; L is the ligand ($AR^5R^6R^7$), as previously defined; n is the integer one or three.

In the above metal coordination complex formulae, only one ligand (L) has to be optically active in order for the process of the reaction to be operable.

If the optical activity of the ligand resides in having an optically active group attached to the phosphorus or arsenic atom, there only has to be one such group, and the other two groups may be the same or inactive. In this instance, only one of the groups $R^5$, $R^6$ or $R^7$ has to be optically active, the remaining two groups may be identical or inactive.

Catalysts which may be used include, but are not limited to, coordination complexes of the following formulae. In the formulae, an asterisk indicates asymmetry, and therefore optical activity. The asterisk denotes the asymmetric atom or dissymmetric group. As an example: $R^*$ indicates a dissymmetric group; $A^*$ indicates the phosphorus or arsenic is asymmetric. Absence of an asterisk indicates no optical acitivity.

(i) $M^1X(A^*R^5R^6R^7)_3$
(ii) $M^1X(A^*R^5R^6R^7)_2(AR^5R^6R^7)$
(iii) $M^1X(A^*R^5R^6R^7)(AR^5R^6R^7)_2$
(iv) $M^1X(AR^{*5}R^6R^7)_3$
(v) $M^1X(AR^{*5}R^6R^7)_2(AR^5R^6R^7)$
(vi) $M^1X(AR^{*5}R^6R^7)(AR^5R^6R^7)_2$
(vii) $M^1X_3(A^*R^5R^6R^7)_3$
(viii) $M^1X_3(A^*R^5R^6R^7)_2(AR^5R^6R^7)$
(ix) $M^1X_3(A^*R^5R^6R^7)(AR^5R^6R^7)_2$
(x) $M^1X_3(AR^{*5}R^6R^7)_3$
(xi) $M^1X_3(AR^{*5}R^6R^7)_2(AR^5R^6R^7)$
(xii) $M^1X_3(AR^{*5}R^6R^7)(AR^5R^6R^7)_2$
(xiii) $M^2X_2(A^*R^5R^6R^7)_2$
(xiv) $M^2X_2(A^*R^5R^6R^7)(AR^5R^6R^7)$
(xv) $M^2X_2(AR^{*5}R^6R^7)_2$
(xvi) $M^2X_2(AR^{*5}R^6R^7)(AR^5R^6R^7)$ wherein $M^1$, $M^2$, X, A, $R^5$, $R^6$, and $R^7$ are as previously defined.

It is understood that in the above illustrated list of catalysts, the dissymmetric group can be $R^5$, $R^6$ or $R^7$ and is not restricted to any one group. In addition, there may be a combination of moieties attached to the metal.

Substituents on the phosphorus and arsenic atoms include but are not limited to: methyl, ethyl, propyl, isopropyl, butyl and its isomers, pentyl and its isomers, hexyl and its isomers, heptyl and its isomers, octyl and its isomers, nonyl and its isomers, decyl and its isomers, undecyl and its isomers, dodecyl and its isomers, cyclopropyl, cyclobutyl, cyclopentyl, cyclohexyl, acetonylphenyl, methylphenyl, ethylphenyl, propylphenyl, butylpenyl, dimethylphenyl, trimethylphenyl, diethylphenyl, benzyl, pyrrole, furan, pyridine, thiophene and piperidine.

A list of phosphine and arsines which may be utilized includes but is not limited to: methylethylphosphine, methylisopropylphospine, ethylbutylphosphine, isopropylisobutylphosphine, methylphenylphosphine, ethylphenylphospine, propylphenylphospine, butylphenylphosphine, phenylbenzylphospine, phenylpyrrolephosphine, ethylisopropylisobutylphosphine, methylphenyl-4-methylphenylphosphine, ethylphenyl-4-methylphenylphosphine, methylisopropylphenylphosphine, ethylphenyl-2,4,5-trimethylphenylphosphine, phenylbenzyl-4-dimethylaminophenylphosphine, phenylpyridylmethylphosphine, phenylcyclopentylethylphosphine, cyclohexylmethylisopropylphosphine and the arsenic derivatives of the above.

Although only one optically active group or ligand is required in the coordination catalyst, it is preferred for ease of preparation that all three ligands are the same. It is also preferred that asymmetry reside on either the phosphorus or arsenic atom.

In a preferred embodiment of this process an olefin is selectively hydrogenated in the presence of an optically active coordinated rhodium or iridium complex according to the following equation:

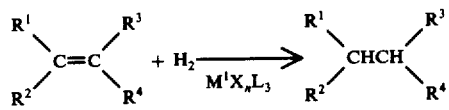

wherein $R^1$, $R^2$, $R^3$ and $R^4$ are each independently selected from the group consisting of hydrogen, alkyl having at least one and a maximum of 6 carbon atoms, substituted alkyl said substituent being selected from the group consisting of amino, hydroxy, nitro, carbonyl, carboxyl, carboxylic ester, said ester group having a maximum of 6 carbon atoms, phenyl, tolyl, xylyl, carboxyl, carboxylic ester, said ester grouping having a maximum of 6 carbon atoms, benzylamino, dibenzylamino and nitro, provided that at least one of the ethylenic carbons on hydrogenation is asymmetric; $M^1$ is selected from the group consisting of rhodium and iridium with rhodium being preferred; X is selected from the group consisting of hydrogen, fluorine, bromine, chlorine and iodine; L is the ligand $AR^5R^6R^7$ wherein $R^5$, $R^6$, $R^7$ is each independently selected from the group consisting of hydrogen, alkyl having a maximum of 12 carbon atoms, phenyl, benzyl, tolyl, xylyl, cycloalkyl having at least 3 and a maximum of 6 carbon atoms, pyrryl, thienyl, furyl, pyridyl, piperidyl, substituted alkyl said substituent being selected from the group consisting of carbonyl, amino and alkoxy having a maximum of two carbons, provided that the groups so selected give an optically active ligand as previously described.

The hydrogenation reaction is usually conducted in a solvent, such as benzene, ethanol, toluene, cyclohexane, and mixtures of these solvents. Almost any aromatic or saturated alkane or cycloalkane solvent, which is inactive to the hydrogenation conditions of this reaction, can be used. Since the hydrogenation reaction of this reaction is specific, solvents such as nitrobenzene can also be utilized. The preferred solvent system is a mixture of a polar and non-polar solvent.

The catalyst is added to the solvent either as a compound per se or as its components which then form the catalyst in situ. When the catalyst is added as its components it may be added prior to, or at the same time as the olefin and/or base. Components for the preparation of the catalyst in situ are the metal salt and the phosphine or arsine ligand. The catalyst is usually added in the range of about 0.005% to about 10%, based on the olefin content.

A tertiary base, such as triethylamine, may be added to the reaction mixture in order to combine with any HCl formed from the hydrogenation of the catalyst. When a base is used, it is added to the reaction mixture in the range of about 0.1% to about 2%, based on the olefin content.

After addition of the components to the solvent, hydrogen is added to the mixture until about 2 to about 5 times the mole quantity of olefin has been added. The pressure of the system will necessarily vary since it will be dependent upon size of hydrogenation apparatus, amount of components and amount of solvent. The initial gauge pressure, however, should be at least about 250 psi. Lower pressures, including atmospheric pressure, can be used, but said lower pressures may result in a slower rate of hydrogenation.

Reaction temperatures may be in the range of about 25° C. to about 100° C. Higher temperatures may be used but are normally not required and may lead to an increase of side reaction and loss in selectiveness.

It should be pointed out that although this invention is directed mainly to asymmetric hydrogenation, the catalyst can also be used in the selective hydrogenation of any olefin whether or not an optically active compound would result. The selectiveness is, therefore, not restricted to olefins which give optically active products.

Upon completion of the reaction which is determined by conventional means, the solvent is removed and the products and catalyst separated by conventional means.

Many natural products and medications exist in an optically active form. In these cases only one of the forms is usually effective. Synthetic preparations of these compounds in the past has required an additional step of separating the products into its entiomorphs. This process is expensive and time consuming. The process of the present invention permits the formation of optically active products thus eliminating much of the time consuming and expensive separation of entiomorphs. Natural products such as the amino acids and flavoring agents can be asymmetrically prepared by this method. An example of this is given in Example 3 in which α-phenylacrylic acid is hydrogenated by the process of this invention to hydratropic acid, which is then reduced to the aldehyde or alcohol, both of which are fragrances, by conventional means.

Amino acids can be prepared by reducing preferably a dibenzylamino compound by the process of this invention and then removing the dibenzyl groups by conventional means to yield the free amino group.

The following examples are illustrative only and the invention is not limited to them. In the following examples "parts" are by weight unless otherwise indicated.

EXAMPLE 1

The optically active phosphines and arsines are prepared according to the procedure of Mislow and Korpiun, J. Am. Chem. Soc. 89, 4784 (1967).

To a suitable vessel equipped with a stirring means, a temperature measuring means and a material addition means was charged 250 parts phenyldichlorophosphine, 240 parts pyridine and 495 parts hexane. The solution was cooled to about 5°-10° C. and a mixture consisting of 96 parts methanol and 27 parts hexane was added, with stirring, over a period of about 1½ hours. The resultant mixture was stirred for an additional 2½ hours as it warmed to about 25° C. This reaction was conducted in an inert nitrogen atmosphere.

Pyridine hydrochloride, formed during the reaction, was filtered and the filtrate concentrated. The yellow residue was distilled, collecting a colorless fraction boiling at 95.5°-97° C./17 mm (82% yield) [Harwood & Grisley, J. Am. Chem. Soc., 82, 423 (1960)]

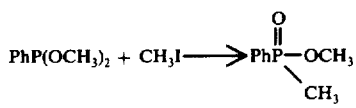

To a suitable vessel equipped with a stirring means, a temperature measuring means and a material addition means was charged 11 parts dimethyl phenylphosphonite, 2.5 parts methyl iodide and 9 parts toluene. The resulant solution was slowly heated. The reaction is exothermic and the temperature increases to about 110° C., the reaction mixture is maintained at a temperature of about 100°-120° C., and an additional 185 parts dimethylphenylphosphonite slowly added. Additional amounts of methyl iodide, in about 1 part increments, are occasionally added during the phosphonite addition. The reaction mixture was maintained at about 110° C. for an additional hour following the addition of components. The reaction mixture was then distilled collecting the portion boiling at 148°-149° C./17 mm (96% yield). [Harwood & Grisley, J. Am. Chem. Soc., 82, 423 (1960)]

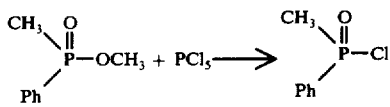

To a suitable vessel equipped with a stirring means, a condensing means, temperature measuring means and a material addition means, was charged 187 parts methyl phenyl (methyl) phosphinate and 1600 parts carbon tetrachloride. To this mixture was added 229 parts phosphorus pentachloride in three portions of 50 parts and one portion of 79 parts. A temperature rise was observed on the addition of the first three portions. The mixture was stirred at about 60° C. for 2 hours and then the carbon tetrachloride and phosphorous oxychloride removed by distillation. The residue was distilled collecting the fraction boiling at 138-141° C./17mm (95% yield). [Methoden Der Organishen Chemie (Houben-Weyl) Vol. XII/I P. 243]

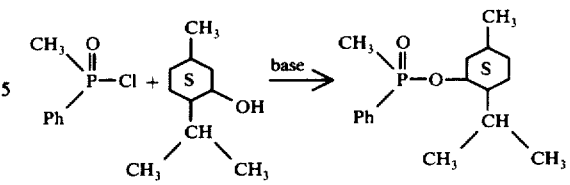

To a suitable vessel equipped with a stirring means, a condensing means, a temperature measuring means, and a material addition means, was added 78 parts l-menthol and 72 parts diethyl ether. To the resultant solution was added 119 parts of triethylamine and the resultant mixture cooled to about 0° C. To this mixture was added, with stirring, 87 parts methylphenylphosphine chloride over a period of about 1½ hours while maintaining the temperature at about 0° C. The mixture was allowed to warm to about 25° C. and then heated at reflux for about 10¼ hours.

The mixture was filtered to remove the triethylamine hydrochloride and the filtrate concentrated. Pentane was added to the residue and the mixture filtered. The filtrate was then concentrated yielding a solid melting at 50°-65° C.

Material recrystallized several times from hexane, then diethyl ether yielded solid melting at 78°-82° C.

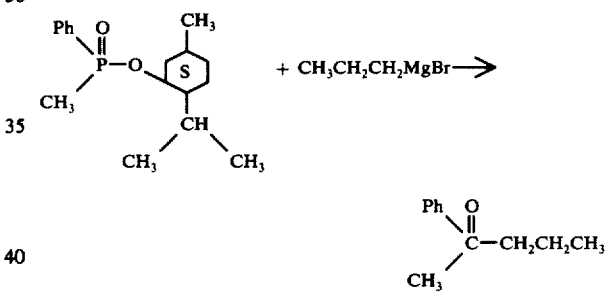

To a suitable vessel equipped with a stirring means, temperature measuring means, material addition means and a condenser means, under an inert nitrogen atmosphere, was added 9.5 parts magnesium, 7 parts diethyl ether and a reaction initiating amount of iodine. A small amount of bromopropane was added to initiate the reaction and then a mixture consisting of 47 parts bromopropane and 123 parts diethyl ether was slowly added at a rate to maintain gentle refluxing of the reaction mixture. The reaction mixture was then cooled to about 25° C. and stirred for an additional 2 hours.

To this mixture was added a mixture consisting of 12 parts methyl methylphenylphosphinate (prepared above) and 88 parts benzene. The diethyl ether was then removed and the resultant mixture heated at 78° C. for 64 hours.

The reaction mixture was decomposed with a solution of ammonium chloride and then filtered. The precipitate was extracted with hot benzene and the extract combined with the filtrate. The organic layer was dried over sodium sulfate and the solvents removed yielding a yellow oil. The oil was chromatographed on a silica gel column with a hexane:benzene:diethyl ether (3:1:1) mixture to yield the product in a 61% yield.

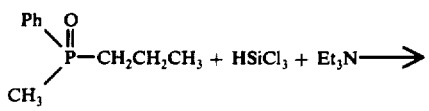
+ HSiCl₃ + Et₃N ⟶

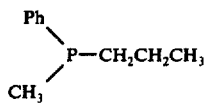

To a suitable vessel, having an inert nitrogen atmosphere, equipped with a stirring means, temperature measuring means, and a material addition means, was charged 16 parts trichlorosilane and 88 parts benzene at a temperature of about 0° C. To this mixture, at a temperature of about 4°–6° C. was added a mixture consisting of 22 parts triethylamine and 44 parts benzene. The resultant mixture was then warmed to about 25° C. and a mixture consisting of 0.82 parts phenyl methylpropylphosphine oxide and 22 parts benzene was added. The mixture was then heated to about 60° C. over a 2-hour period and then cooled to about 25° C.

The reaction mixture was decomposed with 75 parts of a 20% solution of sodium hydroxide followed by 35 parts of water. The resultant mixture was allowed to stand for about 15 hours and then the layers separated. The organic layer was then extracted with 5% hydrochloric acid, twice with water and then dried over sodium sulfate. The solvent was then removed by distillation yielding the product in a 95% yield and having a 69% optical purity.

EXAMPLE 2

Preparation of rhodium III chloride tri-(methylpropylphenylphosphine)

To a suitable vessel, having a nitrogen atmosphere, was charged 0.342 gms (0.0013 moles) of rhodium III chloride trihydrate and 10 ml methanol. To this was added dropwise over a 15 minute period, 0.76 gms (0.0046 moles) of methylpropylphenylphosphine (prepared in Example 1) in 3 ml of methanol. The mixture was allowed to stand for 1 hour during which time a yellow precipitate separated from the solution. The precipitate was removed by filtration yielding 0.21 gms having a specific rotation $[\alpha]_D^{25} = -69.3$. (A)

Concentration of the filtrate yielded an additional 0.13 gms of product having a specific rotation $[\alpha]_D^{25} = -56.4$. (B)

EXAMPLE 3

Asymmetric hydrogenation of α-phenylacrylic acid

To a hydrogenation apparatus equipped with a pressure gauge, thermocouple and heating means, was charged 3 parts α-phenylacrylic acid, 0.021 parts catalyst B (prepared in Example 2), 10 parts benzene, 10 parts ethanol and 0.01 parts triethylamine.

The apparatus was purged and pressurized with hydrogen to a gauge reading of 350 psi of (0.051 moles). The reaction vessel is then heated to 60° C. and shaken for 5 hours, during which time there was a decrease in pressure of 110 psi which is equivalent to the theoretical amount of hydrogen required for reaction.

The reaction mixture was dissolved in 10% sodium hydroxide and the resultant aqueous mixture extracted with ether or ether and benzene to remove the catalyst. The aqueous mixture was then acidified with concentrated hydrochloric acid and extracted with ether. The ether extract was dried over anhydrous sodium sulfate, concentrated and the residue distilled collecting the portion boiling at 91°–92° C./0.2 mm. This fraction in ethanol had a specific rotation $[\alpha]_D^{25} + 12.2°$. This amounts to a 15% optical purity (22% based on the optical purity of the catalyst).

Repeating the reaction using catalyst A (prepared in Example 2) yielded a product having a 14% optical purity.

The reaction was repeated using a non-optically active rhodium III chloride-phosphine catalyst. This reaction yields a non-optically active product.

Reduction of the carboxyl group by known methods to either the aldehyde or alcohol gives rise to the known fragrances hydrotropic aldehyde and hydratropic alcohol.

EXAMPLES 4–11

Other optically active compounds prepared by the process of this invention are as follows:

| Ex. | Olefin | Product | Catalyst | Solvent | Base | Temperature °C Initial Pressure (psi) | Product Observed mp or bp |
|---|---|---|---|---|---|---|---|
| 4 | (CH₃)(CH₃)C=C(H)(COOH) | CH₃CH₂CHCOOH (with CH₃, *) | RhCl₃[PhP(CH₃)(C₃H₇)]₃ | φH:EtOH 1:1 | (C₂H₅)₃N | 60/400 | bp 89–93° C/25mm |
| 5 | CH₂=C(CH₂COOH)(COOH) | CH₃CHCOOH (with CH₂COOH, *) | RhCl₃[PhP(CH₃)(C₃H₇)]₃ | φH:EtOH 1:1 | (C₂H₅)₃N | 25/350 | mp 114–115° C |
| 6 | CH₂=C(CH₂COOH)(COOH) | CH₃CHCOOH (with CH₂COOH, *) | RhCl₃[P(PhC₂H₅)(CH₃)(C₂H₄OCH₃)]₃ | φH:EtOH 1:1 | — | 60/350 | mp 113–114° C |

-continued

| Ex. | Olefin | Product | Catalyst | Solvent | Base | Temperature °C Initial Pressure (psi) | Product Observed mp or bp |
|---|---|---|---|---|---|---|---|
| 7 | $CH_2=C(CH_2COOH)(COOH)$ | $CH_3\overset{*}{C}H(CH_2COOH)(COOH)$ | $RhCl_3[P(CH_2\overset{*}{C}HCH_2CH_3)_3]_3$ | φH:EtOH 1:1 | $(C_3H_7)_3N$ | 25/445 | mp 113.5–114° C |
| 8 | 3-methylcyclohex-2-enone | 3-methylcyclohexanone (*CH₃) | $RhCl_3 \cdot 3H_2O$ + $PhP(CH_2\overset{*}{C}HCH_2CH_3)_2$ with $CH_3$ | φH:EtOH 1:1 | $(C_2H_5)_3N$ | 50/250 | bp 73–74° C/27mm |
| 9 | $CH_2=C(Ph)(OCCH_3{=}O)$ | $CH_3\overset{*}{C}H{-}OCCH_3$ (Ph, =O) | $RhCl_3 \cdot 3H_2O$ + $\phi_2P{-}O{-}$Cholesteryl | φH:EtOH 1:1 | $(C_2H_5)_3N$ | 25/360 | bp 56–58° C/0.9mm |
| 10 | $PhC{\equiv}CH_2$, $CH_2CH_3$ | $Ph\overset{*}{C}HCH_3$, $CH_2CH_3$ | $RhBr[\phi\overset{*}{P}(CH_2CH_3)(N\text{-pyridyl})]_3$ | φH:MeOH 1:1 | — | 45/325 | bp 173° C |
| 11 | $(CH_3)_2C{=}CH{-}COOH$ (actually $CH_3, CH_3, H, COOH$) | $CH_3CH_2\overset{*}{C}H(CH_3)COOH$ | $RhCl_3[Ph\overset{*}{As}(CH_3)(C_3H_7)]_3$ | φH:EtOH 1:1 | — | 60/350 | bp 89–92° C/25mm |

While the illustrative embodiments of the invention have been described hereinbefore with particularly, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

What is claimed is:

1. An optically active metal coordination complex of the formula $M^1X_nL_3$ wherein $M^1$ is rhodium, X is selected from the group consisting of hydrogen, chlorine, fluorine, bromine and iodine, n is one of the integers one or three; each L is independently selected from the group $AR^5R^6R^7$, wherein A is selected from the group consisting of phosphorus and arsenic and $R^5$, $R^6$ and $R^7$ are each independently selected from the group consisting of hydrogen; alkyl having at least one carbon atom and a maximum of 12 carbon atoms; substituted alkyl, said substitution selected from the group consisting of amino, carbonyl, phenyl, nitro and alkoxy, said alkoxy having a maximum of 4 carbon atoms; phenyl; substituted phenyl, said substitution selected from the group consisting of alkyl having a maximum of 4 carbon atoms, amino and nitro, said substitution being less than 3 substituents; cycloalkyl having at least 3 carbon atoms and a maximum of 6 carbon atoms; pyrryl; thienyl; furyl; pyridyl and piperidyl, provided that at least one L group is optically active.

2. A compound in accordance with claim 1 in which A is phosphorus, $R^5$ is phenyl and $R^6$ are each alkyl.

3. A compound in accordance with claim 2 in which $R^6$ is methyl and $R^7$ is propyl.

4. A compound in accordance with claim 2 in which $R^6$ and $R^7$ are 2-methylbutyl.

5. A coordination metal complex, capable of homogeneously catalyzing the hydrogenation of an olefin, comprising a metal selected from the group consisting of rhodium; iridium and ruthenium and a phosphine or arsine ligand wherein at least one phosphine or arsine ligand is optically active.

6. A catalyst according to claim 5 wherein the metal is rhodium.

7. A catalyst according to claim 6 wherein the optically active ligand is a phosphine.

* * * * *

UNITED STATES PATENT OFFICE
CERTIFICATE OF CORRECTION

Patent No. 4,119,652                    Dated October 10, 1978

Inventor(s) William S. Knowles et al.

It is certified that error appears in the above-identified patent and that said Letters Patent are hereby corrected as shown below:

The term of this patent subsequent to November 7, 1995 has been disclaimed.

Signed and Sealed this

Twenty-eighth Day of November 1978

[SEAL]

Attest:

RUTH C. MASON
Attesting Officer

DONALD W. BANNER
Commissioner of Patents and Trademarks

UNITED STATES PATENT AND TRADEMARK OFFICE
CERTIFICATE OF CORRECTION

PATENT NO. : 4,119,652
DATED : October 10, 1978
INVENTOR(S) : William S. Knowles and Milton J. Sabacky It is certified that error appears in the above-identified patent and that said Letters Patent are hereby corrected as shown below:

Column 1, line 8, "1958" should be corrected to read -- 1968 --.

Column 8, line 39, "hydrotropic" should be corrected to read -- hydratropic --.

Column 9, line 37, "particularly" should be corrected to read -- particularity --.

Column 10, line 46 (Claim 2), after "$R^6$" there should be added -- and $R^7$ --.

Signed and Sealed this

Third Day of April 1979

[SEAL]

Attest:

RUTH C. MASON
Attesting Officer

DONALD W. BANNER
Commissioner of Patents and Trademarks